(12) United States Patent
Sadeghi et al.

(10) Patent No.: US 7,400,405 B2
(45) Date of Patent: Jul. 15, 2008

(54) PESTICIDE DETECTOR AND METHOD

(75) Inventors: Darius Akbar Sadeghi, Carmel, CA (US); Herbert L. Berman, Los Altos Hills, CA (US)

(73) Assignee: Bio-Chek LLC, Carmel, CA (US)

( * ) Notice: Subject to any disclaimer, the term of this patent is extended or adjusted under 35 U.S.C. 154(b) by 340 days.

(21) Appl. No.: 11/062,048

(22) Filed: Feb. 18, 2005

(65) Prior Publication Data
US 2006/0187449 A1    Aug. 24, 2006

(51) Int. Cl.
*G01N 21/25* (2006.01)
(52) U.S. Cl. .................................................. 356/417
(58) Field of Classification Search .............. 356/417; 250/910
See application file for complete search history.

(56) References Cited

U.S. PATENT DOCUMENTS

| | | | |
|---|---|---|---|
| 4,666,672 A | 5/1987 | Miller et al. | |
| 4,771,006 A | 9/1988 | Miller et al. | |
| 4,945,250 A * | 7/1990 | Bowen et al. | 250/461.1 |
| 5,166,813 A | 11/1992 | Metz | |
| 5,474,910 A * | 12/1995 | Alfano | 435/34 |
| 5,523,573 A * | 6/1996 | Hanninen et al. | 250/459.1 |
| 5,846,753 A | 12/1998 | Akkara et al. | |
| 5,994,707 A | 11/1999 | Mendoza et al. | |
| 6,031,233 A * | 2/2000 | Levin et al. | 356/326 |
| 6,052,187 A * | 4/2000 | Krishnan et al. | 356/364 |
| 6,343,168 B1 | 1/2002 | Murphy et al. | |
| 6,571,118 B1 | 5/2003 | Utzinger et al. | |
| 6,792,395 B2 | 9/2004 | Roberts | |
| 2003/0048445 A1* | 3/2003 | Tokhtuev et al. | 356/409 |
| 2003/0103199 A1* | 6/2003 | Jung et al. | 356/419 |
| 2003/0160182 A1* | 8/2003 | Petrich et al. | 250/458.1 |
| 2003/0173525 A1* | 9/2003 | Seville | 250/458.1 |
| 2004/0011965 A1* | 1/2004 | Hodgkinson | 250/461.1 |
| 2004/0130714 A1* | 7/2004 | Gellerman et al. | 356/300 |
| 2004/0199079 A1* | 10/2004 | Chuck et al. | 600/477 |
| 2005/0030533 A1* | 2/2005 | Treado | 356/318 |

OTHER PUBLICATIONS

Booksh, Excitation Emission Matrix Fluorescence, Booksh Group Home Page, Arizona State University, www.public.asu.edu/booksh/eem.htm, Jan. 14, 2005.

C & L Instruments, Inc., Optics of a Fluorescence Microscope, www.fluorescence.com/tutorial/fm-optic.htm, no date.

Freudenrich, Fluorescence Microscopy, How Light Microscopes Work, www.science.howstuffworks.com/light-microscope4.htm, no date.

(Continued)

*Primary Examiner*—Kara E Geisel
(74) *Attorney, Agent, or Firm*—Edward S. Wright

(57) ABSTRACT

Highly portable, handheld instrument which can be pointed at the produce to be checked. Light from a source within the instrument is directed onto the produce to induce fluorescent emission from the produce, and fluorescent emissions from the produce are monitored with a detector within the instrument to detect the presence of pesticide residue on the produce. The light from the source is filtered to selectively pass light of a wavelength which induces maximum fluorescent emission from the pesticide to be detected, and the emissions from the produce are filtered to selectively pass emissions having a spectral content characteristic of the pesticide to be detected.

18 Claims, 5 Drawing Sheets

OTHER PUBLICATIONS

Jiji et al., Excitation-Emission Matrix Fluorescence based Determination of Carbamate Pesticides and Polycyclic Aromatic Hydrocarbons, Analytica Chimica Acta 397, 1999, 61-72.

Jiji et al., Application of PARAFAC for Calibration with Excitation-Emission Matrix Fluorescence Spectra of Three Classes of Environmental Pollutants, Journal of Chemometrics, 2000.

* cited by examiner

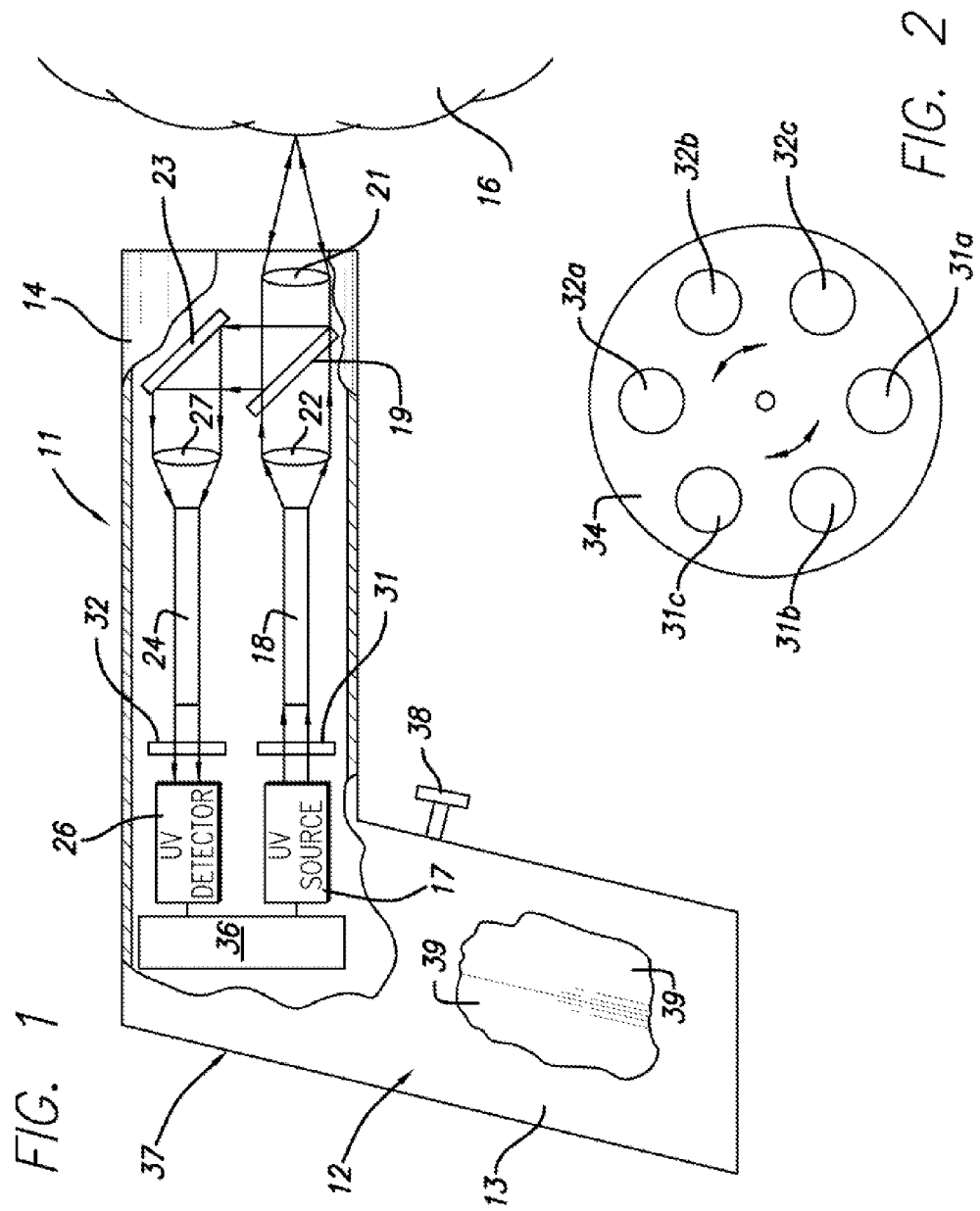

PESTICIDE DETECTOR AND METHOD

BACKGROUND OF THE INVENTION

1. Field of Invention

This invention pertains generally to the detection of pesticides and, more particularly, to a handheld instrument and method which are particularly suitable for detecting pesticides on lettuce and other produce.

2, Related Art

Organic farming has been one of the fastest growing segments of American agriculture in recent years, and many people prefer organic produce because of its superior taste and quality. Organic farmers are not allowed to use synthetic pesticides or fertilizers, and organically grown produce contains significantly lower levels of pesticide residues than conventionally grown produce. With its more stringent growing requirements, popularity among consumers, and relatively limited availability, organic produce generally commands a higher price than conventional produce.

Organic produce is currently checked for pesticide residue by washing the produce with water and then sending a sample of the water to a laboratory for analysis. That is a time consuming and expensive process and one which is not suitable for in situ checking to see if a given load of produce has, in fact, been organically grown.

Heretofore, there have been some attempts to provide portable instruments for checking produce for the presence of pesticide residue through fluorescence spectroscopy in the field. Such attempts still require the use of an aqueous sample which is placed in a cuvette and analyzed in a spectrometer. While such instruments avoid the need to send the sample to a laboratory, the use of the aqueous sample is still time consuming and cumbersome.

OBJECTS AND SUMMARY OF THE INVENTION

It is, in general, an object of the invention to provide a new and improved instrument and method for detecting pesticides on lettuce and other produce.

Another object of the invention is to provide an instrument and method of the above character in which the instrument is highly portable and handheld.

These and other objects are achieved in accordance with the invention by providing a highly portable, handheld instrument which can be pointed at the produce to be checked, directing light from a source within the instrument onto the produce to induce fluorescent emission from the produce, and monitoring fluorescent emissions from the produce with a detector within the instrument to detect the presence of pesticide residue on the produce. The light from the source is filtered to selectively pass light of a wavelength which induces maximum fluorescent emission from the pesticide to be detected, and the emissions from the produce are filtered to selectively pass emissions having a spectral content characteristic of the pesticide to be detected.

BRIEF DESCRIPTION OF THE DRAWINGS

FIG. 1 is a side elevational view, partly broken away and somewhat schematic, of one embodiment of a handheld instrument for detecting pesticides on produce in accordance with the invention.

FIG. 2 is a side elevational view of a filter wheel for use in the embodiment of FIG. 1.

DETAILED DESCRIPTION

Figure 3:
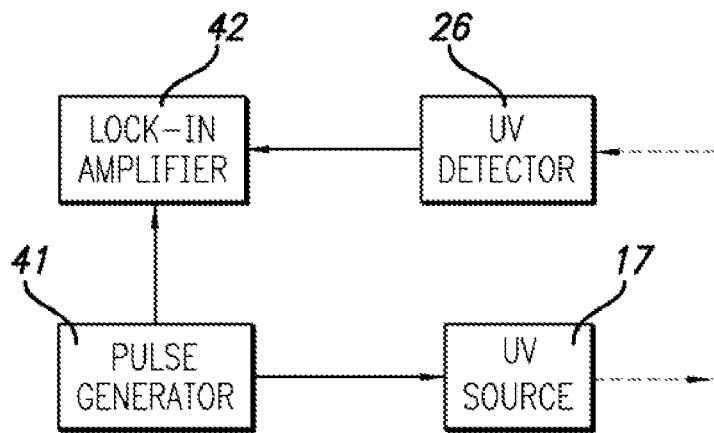
FIG. 3 is a simplified block diagram of the embodiment of FIG. 1.

In the embodiment illustrated in FIG. 1, the instrument 11 has a housing 12 in the shape of a pistol, with a grip 13 which can be held in the hand of a user and a barrel 14 which can be pointed at produce 16 which is to be checked for the presence of pesticide residue. The produce can, for example, be a head of lettuce, an apple or any other fruit or vegetable.

An excitation source 17 is mounted within the housing for generating light which is directed onto the produce to induce fluorescent emission having a spectral content characteristic of the material that is emitting it. In the presently preferred embodiment, the light source is a mercury vapor lamp which emits ultra-violet (UV) light at wavelengths of 254, 315 and 365 nanometers (nm). The light source is located toward the rear of the barrel.

A bundle of one or more optical fibers 18 extends down the barrel from the light source toward a dichroic filter 19 and a focusing lens 21 near the front of the barrel, with another lens 22 between the fibers and the filter. The light passes through the dichroic filter and is focused on the target by the lenses.

The dichroic filter is reflective to the fluorescent emissions from the target, and those emissions are directed onto a mirror 23 which is positioned to one side of the filter near the front of the barrel.

A second bundle of one or more optical fibers 24 extends down the barrel from the mirror toward a UV detector 26, with a lens 27 between the mirror and the optical fibers for focusing emissions reflected by the mirror onto the fibers. The detector is located toward the rear of the barrel near the source.

Both the light from the source and the emissions from the target are filtered in order to maximize the emissions from the target and to make the instrument selectively responsive to emissions having a spectral content which is characteristic of the pesticide or pesticides to be detected. For that purpose, a first filter 31 is positioned between excitation source 17 and optical fibers 18, and a second filter 32 is positioned between optical fibers 24 and detector 26. Filter 31 is selected to pass light at a wavelength which induces the maximum fluorescent emission from the target for the pesticide to be detected, and filter 32 is selected to selectively pass emissions having a spectral content which is characteristic of that pesticide.

To detect different pesticides, a plurality of filters are mounted in pairs on a wheel 34 or other suitable carrier which can be moved to bring the filters for the desired pesticide into registration with the light source and detector. Thus for example, to detect the carbamate pesticides carbaryl, 1-Naphthol, and carbofuran, three sets of filters 31*a*-31*c* and 32*a*-32*c* can be provided. For carbaryl, the excitation maximum is near 270 nm and the emissions peak is around 320 nm, and filters 31*a* and 32*a* have passbands centered at those wavelengths. With 1-Naphthol the excitation maximum is near 280 nm, the emissions peak is around 340 nm, and filters 31*b* and 32*b* are centered at those wavelengths. For carbofuran, the excitation maximum is near 270 nm, the emissions peak is near 300 nm, and filters 31*c* and 31*d* are centered at those wavelengths.

Electronic circuitry 36 associated with the light source and the detector is mounted in the housing to the rear of the light source and detector. A display 37 for readings taken by the instrument is located at the rear of the barrel, and a trigger operated switch 38 for initiating readings is located in front of the grip. Memory for storing the readings is included in the circuitry, and batteries 39 for powering the instrument are mounted in the grip.

In the embodiment illustrated in FIG. 3, circuitry 36 includes a pulse generator or clock 41 for controlling the operation of excitation source 17 to provide a pulsating light for exciting the target and a lock-in amplifier 42 for processing the signals from emissions detector 26. The clock signals or pulses which control the source are also applied to the reference input of the lock-in amplifier so that the detector output is, in effect, sampled in synchronization with the light from the source. This provides a high signal-to-noise ratio, particularly if the pulse rate is not an integral multiple of the local power line the frequency. Thus, for example, with 60 Hz power lines, a pulse rate of 90 Hz would be suitable.

Figure 4:
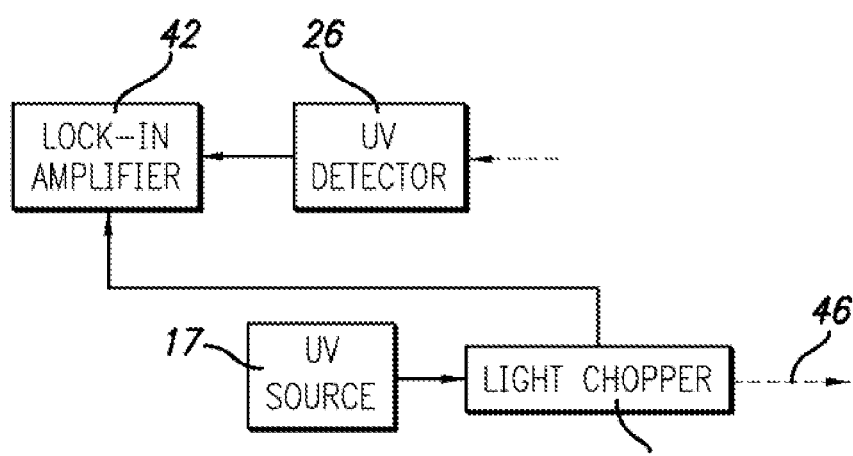
FIG. 4 is a simplified block diagram of another embodiment of a handheld instrument for detecting pesticides on produce in accordance with the invention.

In the embodiment of FIG. 4, the excitation source delivers a steady light output which is passed through a chopper 44 to produce a pulsating beam 46 that is directed onto the target. Signals from the emissions detector are processed by a lock-in amplifier 47 which is synchronized with the chopper to provide a high signal-to-noise ratio.

A pulsating beam can also be produced by the use of a stroboscopic source such as a Xenon flash lamp which produces one or more pulses of light.

Use of the instrument is simple and straightforward. The filter wheel is rotated to select the filters for the pesticide to be detected, the barrel is pointed at the target, and the trigger is pulled to take a reading. If residue of the pesticide is present, it will produce emissions which will be detected. The presence and/or approximate amount of the pesticide is indicated on the display and stored in memory.

Figure 5:
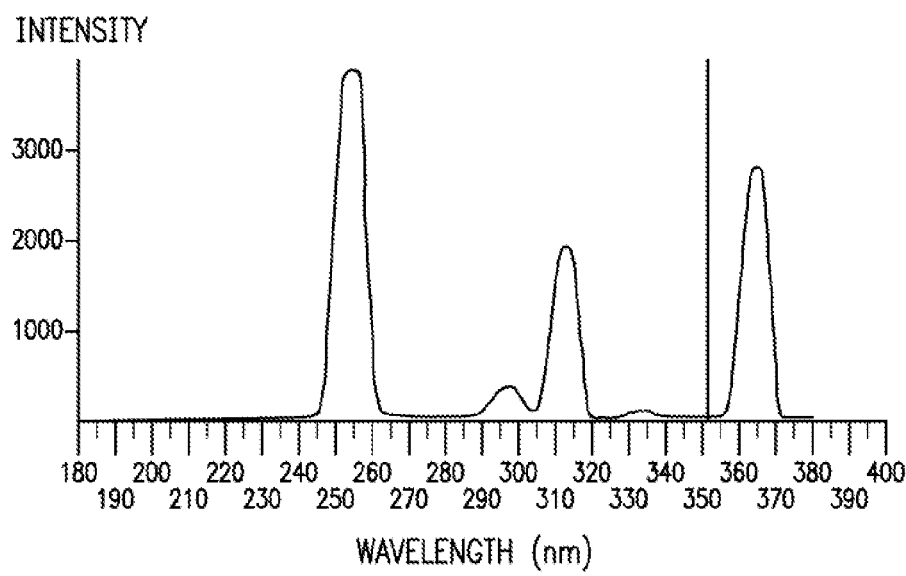
FIGS. 5-9 are response curves illustrating the detection of pesticide residue on produce in accordance with the invention.
Figure 6:
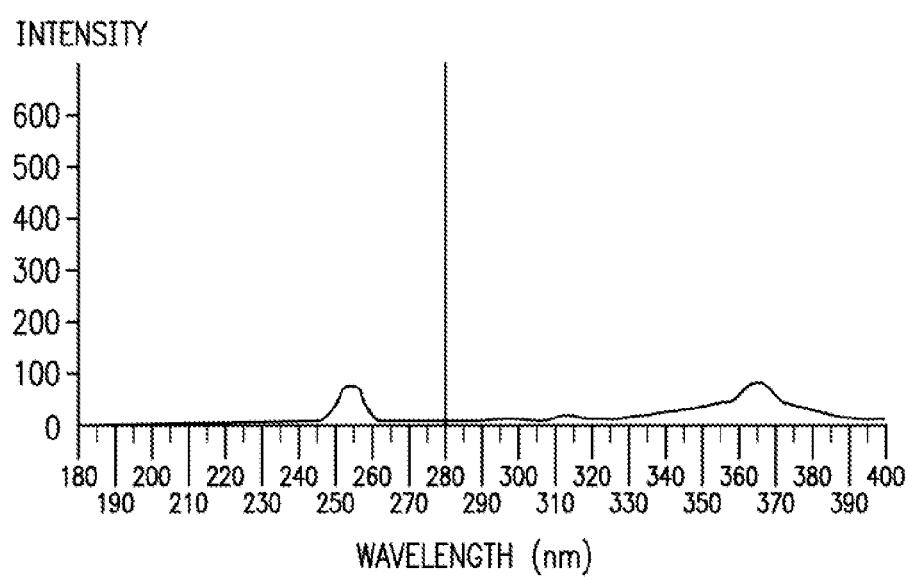
Figure 7:
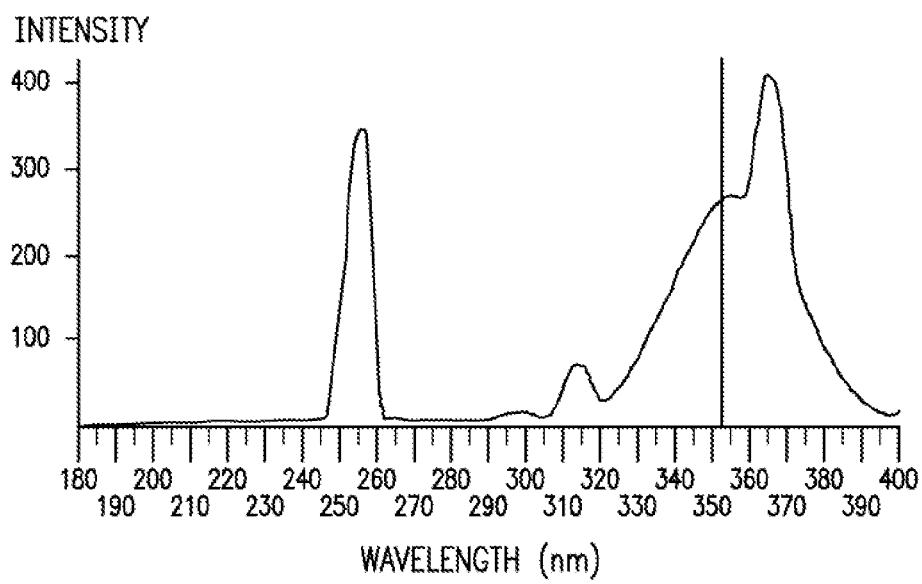
Figure 8:
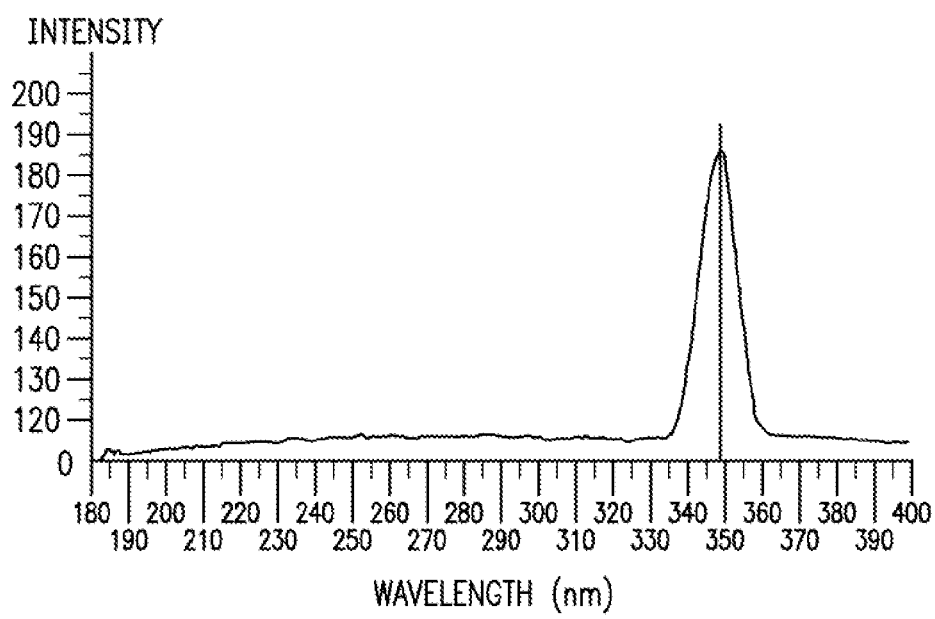
Figure 9:
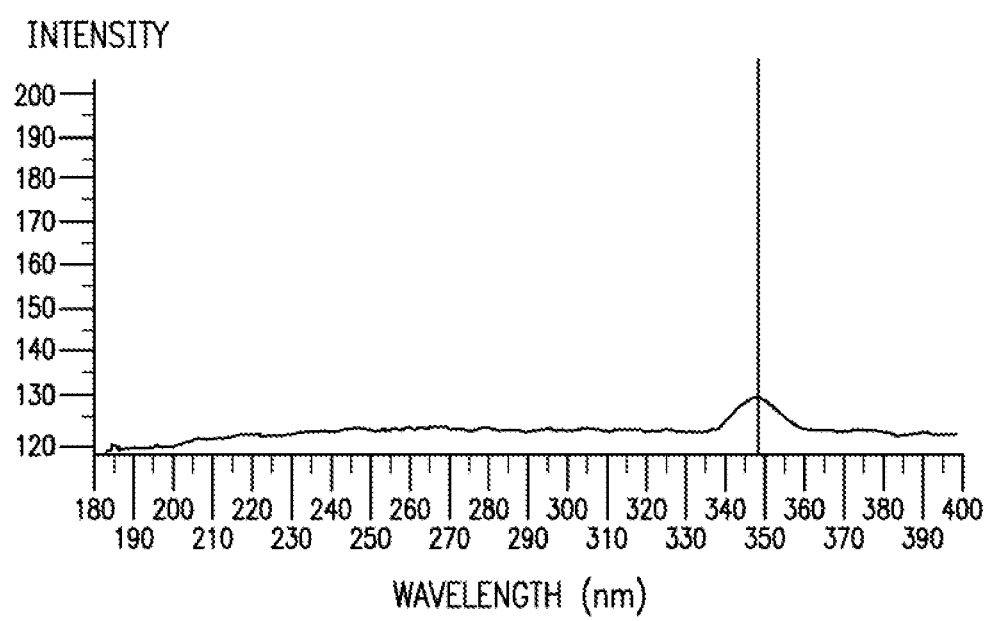

FIG. 5 shows the spectral content of the light from a mercury vapor lamp with peaks at 254 nm, 315 nm and 365 nm. FIG. 6 shows the spectral content of the fluorescent emissions which are produced by green lettuce without pesticide residue when illuminated with light from the mercury vapor lamp. FIG. 7 shows the result with the same light source and a carbamate pesticide, and FIG. 8 shows the result for the carbamate pesticide with a 350 nm filter in front of the detector. FIG. 9 shows the response produced by the green lettuce without pesticide residue with the 350 nm filter in front of the detector.

With the lettuce, there are no significant emissions in the spectrum of interest, and the weak responses centered at 254 nm, 315 nm, and 365 nm which appear in FIG. 6 are believed to be reflections of the excitation light by the lettuce. With the carbamate, the peaks from the source remain, but there is also a strong emission from the carbamate which is centered at about 353 nm. With the filter, everything is removed except the emission from the carbamate. Without the carbamate, the filter eliminates everything from the lettuce except the weak reflection of the excitation light around 350 nm.

The invention has a number of important features and advantages. It provides a highly portable, self-contained, battery powered instrument which can detect the presence of pesticide residue instantly and without contact with the produce. It can be used in the field as well as by distributors and at super markets to determine pesticide content.

It is apparent from the foregoing that a new and improved instrument and method for detecting and identifying pesticides on lettuce and other produce has been provided. While only certain presently preferred embodiments have been described in detail, as will be apparent to those familiar with the art, certain changes and modifications can be made without departing from the scope of the invention as defined by the following claims.

The invention claimed is:

1. A handheld instrument for checking produce for the presence of pesticide residue, comprising: a housing having a grip which can be held in the hand and a barrel which can be pointed at the produce, an excitation source and an emission detector within the housing toward the rear of the barrel, a first group of optical fibers for directing light from the source down the barrel toward the produce to induce fluorescent emission from pesticide residue on the produce, a dichroic filter positioned toward the front of the barrel for transmitting the light toward the produce and reflecting emissions from pesticide residue on the produce, a second group of optical fibers for transmitting the reflected emissions down the barrel toward the detector, a first set of filters for selectively passing light of wavelengths which induce maximum fluorescent emission from different pesticides, a second set of filters for selectively passing emissions having spectral contents characteristic of the different pesticides, and means for selectively bringing the filters in the respective sets for one of the pesticides into registration with the excitation source and the emissions detector.

2. The handheld instrument of claim 1 wherein the filters are mounted on a wheel which can be rotated to bring the filters in the first set into registration with the excitation source and the filters in the second set into registration with the emissions detector.

3. The instrument of claim 1 wherein the light directed toward the produce is pulsating, and the instrument includes means for processing signals from the detector in synchronization with the pulsating light.

4. The instrument of claim 3 including means for pulsing the excitation source to produce the pulsating light.

5. The instrument of claim 3 including means for chopping the light from the source to provide the pulsating beam.

6. The instrument of claim 3 wherein the means for processing signals from the detector includes a lock-in amplifier.

7. An instrument for checking produce for the presence of pesticide residue, comprising: a housing which can be held in hand and pointed at the produce, a light source within the housing, means within the housing for directing light from the source toward the produce to induce fluorescent emission from pesticide residue on the produce, a detector within the housing, means within the housing for directing fluorescent emissions from pesticide residue on the produce toward the detector, a first set of filters for selectively passing light of wavelengths which induce maximum fluorescent emission from different pesticides, a second set of filters for selectively passing emissions having spectral contents characteristic of the different pesticides, and means for selectively bringing the filters for one of the pesticides into registration with the excitation source and the emissions detector.

8. The instrument of claim 7 wherein the detector is responsive to fluorescent emissions having a wavelength on the order of 300 to 340 nm.

9. The instrument of claim 7 wherein the filters in the first set selectively pass light having wavelengths on the order of 270 to 280 nm.

10. The instrument of claim 7 wherein the filters in the second set selectively pass emissions having wavelengths in the range of about 300 to 340 nm.

11. The instrument of claim 7 including circuitry within the housing for processing signals from the detector, and a battery mounted in the housing for powering the light source and the circuitry.

12. The instrument of claim 7 wherein the light source is an ultraviolet source.

13. The instrument of claim 7 wherein the light directed toward the produce is pulsating, and the instrument includes circuitry for processing signals from the detector in synchronization with the pulsating light.

14. The instrument of claim 13 including means for pulsing the light source to produce the pulsating light.

15. The instrument of claim 13 includung means for chopping the light from the source to provide the pulsating beam.

16. The instrument of claim 13 wherein the circuitry for processing signals from the detector includes a lock-in amplifier.

17. The instrument of claim 11 wherein the means for directing light from the source toward the produce and the means for directing emissions from pesticide residue on the produce toward the detector are located in the barrel of the housing.

18. The instrument of claim 17 wherein the means for directing light from the source toward the produce and the means for directing emissions from pesticide residue on the produce toward the detector include light transmissive optical fibers.

* * * * *